(12) United States Patent
Dasai et al.

(10) Patent No.: US 10,309,922 B2
(45) Date of Patent: Jun. 4, 2019

(54) DEVICE FOR DETECTING CHEMICAL/PHYSICAL PHENOMENON

(71) Applicant: National University Corporation Toyohashi University of Technology, Toyohashi-shi, Aichi (JP)

(72) Inventors: Fumihiro Dasai, Toyohashi (JP); Kazuaki Sawada, Toyohashi (JP)

(73) Assignee: NATIONAL UNIVERSITY CORPORATION TOYOHASHI UNIVERSITY OF TECHNOLOGY, Toyohashi-Shi, Aichi (JP)

( * ) Notice: Subject to any disclaimer, the term of this patent is extended or adjusted under 35 U.S.C. 154(b) by 0 days.

(21) Appl. No.: 15/555,740

(22) PCT Filed: Feb. 19, 2016

(86) PCT No.: PCT/JP2016/054965
§ 371 (c)(1),
(2) Date: Sep. 5, 2017

(87) PCT Pub. No.: WO2016/147798
PCT Pub. Date: Sep. 22, 2016

(65) Prior Publication Data
US 2018/0052135 A1 Feb. 22, 2018

(30) Foreign Application Priority Data
Mar. 19, 2015 (JP) .................. 2015-056804

(51) Int. Cl.
*G01N 27/00* (2006.01)
*G01N 27/327* (2006.01)
(Continued)

(52) U.S. Cl.
CPC ......... *G01N 27/3278* (2013.01); *G01N 21/00* (2013.01); *G01N 27/414* (2013.01);
(Continued)

(58) Field of Classification Search
CPC ........... G01N 27/3278; G01N 27/4145; G01N 27/4148; G01N 27/414; G01N 27/403;
(Continued)

(56) References Cited

U.S. PATENT DOCUMENTS 6,294,133 B1 * 9/2001 Sawada .................. G01K 1/045
204/400
7,826,980 B2 11/2010 Sawada et al.
(Continued)

FOREIGN PATENT DOCUMENTS

EP 3246699 A1 11/2017
JP 4171820 B2 8/2008
(Continued)

OTHER PUBLICATIONS

International Search Report for PCT/JP2016/054965, with translation.
(Continued)

*Primary Examiner* — Thang X Le
(74) *Attorney, Agent, or Firm* — Gavin J. Milczarek Desai; Quarles & Brady LLP

(57) ABSTRACT

Proposed is a device for detecting a chemical/physical phenomenon, in which, via a novel scheme, charges are accumulated in a charge accumulation region. An amount of charges thus accumulated reflects the potential of a sensing region and the potential corresponds to an external environment (chemical phenomenon or physical phenomenon) to be detected. A charge accumulation region 5 includes a first potential well region FD1 that is continuous with a sensing region 3, the boundary potential of the charges held in the first potential well region FD1 being made equal to the potential of the sensing region 3, whereby the potential of the sensing region 3 is made to be reflected in the amount of charges held in the first potential well region FD1.

6 Claims, 14 Drawing Sheets

(51) Int. Cl.
  *G01N 27/414* (2006.01)
  *G01N 33/543* (2006.01)
  *H01L 21/768* (2006.01)
  *H01L 23/532* (2006.01)
  *G01N 21/00* (2006.01)
  *H01L 29/78* (2006.01)

(52) U.S. Cl.
  CPC ..... *G01N 27/4145* (2013.01); *G01N 27/4148* (2013.01); *G01N 33/5438* (2013.01); *H01L 21/76883* (2013.01); *H01L 23/53238* (2013.01); *H01L 23/53295* (2013.01); *H01L 29/78* (2013.01)

(58) Field of Classification Search
  CPC ............ G01N 27/4035; G01N 33/5438; H01L 23/53295; H01L 23/53238; H01L 21/76883; H01L 27/14643; H01L 31/062; H01L 31/113
  See application file for complete search history.

(56) References Cited

U.S. PATENT DOCUMENTS

| | | | |
|---|---|---|---|
| 9,970,897 B2 * | 5/2018 | Garcia | G01N 27/4148 |
| 2006/0129332 A1 * | 6/2006 | Mimura | G01N 27/4148 |
| | | | 702/23 |
| 2008/0231253 A1 | 9/2008 | Sawada et al. | |
| 2010/0052080 A1 | 3/2010 | Garcia Tello et al. | |
| 2011/0068372 A1 * | 3/2011 | Ren | G01N 27/414 |
| | | | 257/194 |
| 2012/0000274 A1 | 1/2012 | Fife | |
| 2013/0288378 A1 * | 10/2013 | Gu | G01N 27/4141 |
| | | | 436/37 |
| 2014/0193938 A1 | 7/2014 | Fife | |
| 2014/0200842 A1 | 7/2014 | Dasai et al. | |

FOREIGN PATENT DOCUMENTS

| | | |
|---|---|---|
| JP | 2010-525360 A | 7/2010 |
| JP | 2013-533482 | 8/2013 |
| WO | 2006/095903 | 9/2006 |
| WO | 2013/024791 | 2/2013 |

OTHER PUBLICATIONS

Nakazawa, H. et al., "A Fused pH and Fluorescence Sensor Using the Same Sensing Area", Applied Physics Express, Japan Society of Applied Physics, Apr. 2, 2010, vol. 3, No. 4, pp. 47001-47003, Japan.

European Patent Office, Extended European Search Report for EP Application No. 16764628.0, dated Sep. 7, 2018, 11 pages.

* cited by examiner

DEVICE FOR DETECTING CHEMICAL/PHYSICAL PHENOMENON

TECHNICAL FIELD

The present invention relates to an improvement of a chemical/physical phenomenon detecting device.

BACKGROUND ART

As a chemical/physical phenomenon detecting device, a pH sensor disclosed in Patent Document 1 is known.

In a conventional chemical/physical phenomenon detection device, charges existing in a sensing region are transferred to a charge accumulation region and accumulated therein, the charges thus accumulated are measured to identify chemical phenomenon or physical phenomenon to be detected.

By surrounding the sensing region with a weir of a predetermined potential, a potential difference between the potential of the weir (e.g. TG region) and the potential of the sensing region is proportional to the amount of charges that can be present in the sensing region. Since the potential of the sensing region changes according to the change in the chemical phenomenon or the physical phenomenon (external environment) to be detected, the change in the external environment is reflected in the potential difference between the potential of the sensing region and the potential of the weir. The sensing region can hold an amount of charges corresponding to the environment exists. Charges in the sensing region are transferred to the charge accumulation region by changing the potential of the TG region that is a part of the weir.

PRIOR ART DOCUMENT

Patent Document

Patent Document 1: Japanese Patent No. 4171820
Patent Document 2: Published Japanese Translation No. 2010-525360

SUMMARY OF THE INVENTION

Problems to be Solved by the Present Invention

In the conventional chemical/physical phenomenon detecting device, the potential weir is provided around the sensing region to form a charge pool which holds charges to detect a chemical phenomenon or a physical phenomenon.

The potential of the gate provided in the weir is controlled to supply charges to this charge pool and transferring charges from the charge pool to the charge accumulation region. In general, when supplying charges, the potential of the TG region is fixed while the potential of the ICD region is changed. When transferring charges thereafter, the potential of the TG region is changed while the potential of the ICD region is fixed.

In this way, the conventional chemical/physical phenomenon detecting device requires to control the gate when the charges are injected to the charge pool as well as being ejected from the pool, the device comprises the charge pool in the sensing region and the depth of the charge pool is changed according to the chemical phenomenon or physical phenomenon to be detected, and the amount of charges present in the charge pool is measured. The conventional device thus constructed needs or spends lead times for respective controls and a device for controlling the respective gates is also required.

Means to Solve the Problems

As a result of intensive investigations by the present inventors to solve at least one of the above-mentioned problems, it has been found a novel chemical/physical phenomenon detecting device. The device performs, without using the above-described charge pooling method, a novel method. That is, an amount of charges reflecting a potential of a sensing region defined by the external environment (the chemical phenomenon or physical phenomenon) to be detected is accumulated in a charge accumulation region of the device.

The first aspect of the present invention is defined as follows.

A chemical/physical phenomenon detecting device comprises a semiconductor substrate in which a sensing region and a charge accumulation region are partitioned, a potential of the sensing region changes in accordance with a change in an external environment, and an amount of charges reflecting the potential of the sensing region is accumulated in the charge accumulation region and the accumulated charges are detected, wherein the charge accumulation region comprises a first potential well region formed continuously with the sensing region, and wherein the potential of the sensing region is reflected to an amount of charges held in the first potential well region by setting the boundary potential of the charges held in the first potential well region to be equal to the potential of the sensing region.

Here, the boundary potential of the charges held in the first potential well region means the electric potential of the charges most distant from the electric potential of the first potential well region. For example, when electrons are adopted as the charges, it is the lowest potential of the electrons held in the first potential well region.

According to the chemical/physical phenomenon detecting device of the first aspect defined as above, the boundary potential of the charges held in the first potential well region is made equal to the potential of the sensing region, and the potential of the sensing region is reflected to the amount of charges held in the first potential well region. The amount of charges thus held in the first potential well region is measured to detect a chemical phenomenon or a physical phenomenon as an object to be detected.

Here, no charge pool is formed in the sensing region, so no weir is required so that it is not necessary to provide a gate in the weir. This makes it be unnecessary for a device to control the gate and a lead time for driving the device as conventionally required.

A second aspect of the present invention is defined as follows. That is, in the chemical/physical phenomenon detection device according to the first aspect, the charge accumulation region includes the first potential well region, a second potential well region, and an analog gate region AG positioned between the first potential well region and the second potential well region, wherein charges held in the first potential well region are transferred to the second potential well region by adjusting the electric potential of the AG region, and the amount of charges accumulated in the second potential well region is detected.

According to the chemical/physical phenomenon detecting device of the second aspect defined as above, the charges held in the first potential well region are sequentially transferred to the second potential well region and accumulated therein. The accuracy of detection is thus improved.

A third aspect of the present invention is defined as follows. That is, in the chemical/physical phenomenon detection device according to the second aspect, the semiconductor substrate further comprising;

a charge input region for supplying charges to the sensing region, an input charge control region formed between the charge input region and the sensing region to adjust the supply of charges from the charge input region to the sensing region, and a third potential well region positioned between the input charge control region and sensing region and formed continuously with the sensing region.

According to the chemical/physical phenomenon detecting device of the third aspect defined as above, the sensing region is sandwiched between the first potential well region and the third potential well region. The potential (potential at the bottom) of each potential well region is at a potential that can draw the charge existing in the sensing region, and accordingly, no charge can be present in the sensing region.

In other words, a gate region continuously present in the sensing region causes a potential barrier between them (for details, refer to Patent Document 1). In a case where a potential well region exists between the sensing region and the gate region, the potential barrier disappears. It is, therefore, possible to reliably prevent the charges from remaining in the sensing region.

In the above, the first to third potential well regions are formed by doping impurities into the semiconductor substrate, the potential thereof is stable, and even if no voltage is externally applied, the potential of the well regions can be significantly distinguished form the potential of the sensing region.

A fourth aspect of the present invention is defined as follows. That is,

A method for controlling a chemical/physical phenomenon detecting device, wherein the device comprises a semiconductor substrate in which a sensing region and a charge accumulation region are partitioned, a potential of the sensing region changes in accordance with a change in an external environment, and an amount of charges reflecting the potential of the sensing region is accumulated in the charge accumulation region and the accumulated charges are detected, and wherein the charge accumulation region comprises a first potential well region continuous with the sensing region, the method comprising steps of;

a sensing step for making the boundary potential of charges in the first potential well region equal to the potential of the sensing region; and a detecting step for detecting an amount of the charges held in the first potential well region in the sensing step.

According to the method for controlling the chemical/physical phenomenon detecting device defined in the fourth aspect defined as above, the same effect explained in the first aspect can be performed.

A fifth aspect of the present invention is defined as follows. That is, in the method for controlling the chemical/physical phenomenon detecting device according to the fourth aspect, wherein the charge accumulation region includes the first potential well region, a second potential well region, and an analog gate region AG positioned between the first potential well region and the second potential well region, and wherein the method further comprises an accumulation step for accumulating charges in the second potential well region, the charges are transferred from the first potential well region to the second potential well region by adjusting potential of the AG region, and the charges thus accumulated in the second potential well region are detected in the detecting step.

According to the method for controlling the chemical/physical phenomenon detecting device defined in the fifth aspect described as above, highly accurate detection can be performed as in the second aspect.

A sixth aspect of the present invention is defined as follows. That is, in the method for controlling a chemical/physical phenomenon detecting device defined in the fourth aspect, wherein the charge accumulation region includes the first potential well region, a second potential well region, and an analog gate region AG positioned between the first potential well region and the second potential well region, the semiconductor substrate comprises a charge input region for supplying charges to the sensing region, and an input charge control region formed between the charge input region and the sensing I region to adjust the supply of charges from the charge input region to the sensing region, and the sensing region has photosensitivity, the method comprising the steps of, a step for making absolute potential values of the AG region and the input charge control region to be the input charge control region <the AG region ≤the sensing region.

a step for transferring charges generated in the sensing region according to the incident light to the second potential well region via the AG region.

According to the method for controlling the chemical/physical phenomenon detecting device of the sixth aspect defined as above, it is also possible to detect light intensity by using a device for detecting a chemical phenomenon such as pH.

DETAILED DESCRIPTION OF THE INVENTION

First Embodiment

Figure 1:
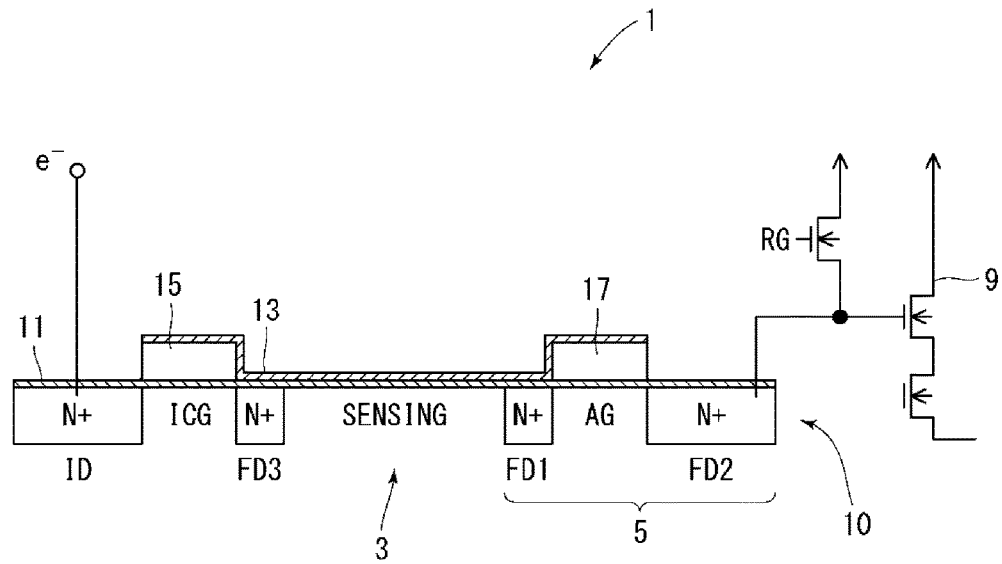
FIG. 1 is a cross-sectional view showing a configuration of a pH sensor 1 according to a first embodiment of the present invention.

FIG. 1 shows the principle configuration of a pH sensor 1 as a chemical/physical phenomenon detection device according to the first embodiment of the present invention.

The pH sensor 1 is comprised of a semiconductor substrate 10 and a structure stacked on the substrate 10.

On the semiconductor substrate 10, a charge input region ID for supplying charges is provided. A second gate region ICG, a third potential well region FD 3, a sensing region 3, a first potential well region FD 1, a first gate region AG and a second potential well region FD 2 are provided and aligned in the semiconductor substrate 10 in a charge flow direction form the ID region.

Ambits or boundaries of each region are defined by a difference in conduction type in the semiconductor substrate 10. For example, when electrons are used as charges, the charge input region ID, the first to third potential well regions FD 1 to FD 3 are n+ type regions, and the second gate region ICG, the first gate region AG, and the sensing region 3 are p-type regions.

A silicon oxide insulation film 11 is stacked on the surface of the semiconductor substrate 10 and an ICG electrode 15 is stacked on the film 11 at a position opposed to the second gate region ICG for controlling a potential of the second gate region ICG. An AG electrode 17 is also stacked on the insulation film at a position opposed to the first gate region AG for controlling a potential of the first gate region AG. A silicon nitride film 13 as a sensitive film is laminated on a portion corresponding to the sensing region 3. Since the silicon nitride film 13 is formed after the ICG electrode 15 and the AG electrode 17, the silicon nitride film 13 also covers these electrodes.

The area and plane shape of each region, the amount of dopant introduced, and the material of the sensitive film can be arbitrarily designed in consideration of the object to be measured, measurement conditions, required sensitivity, and the like.

Figure 2:
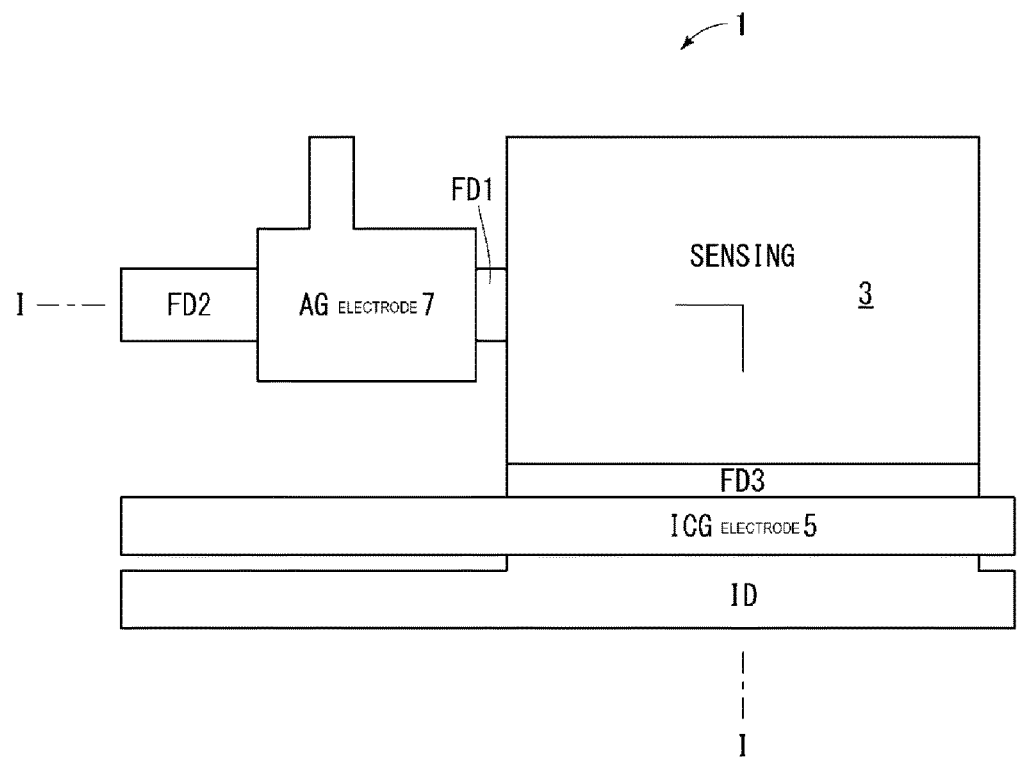
FIG. 2 shows a planar structure of the pH sensor 1.

FIG. 2 shows the planar structure of the pH sensor 1. As shown in the example of FIG. 2, a rectangular sensing region 3 is adopted, and a third potential well region FD 3—a second gate region ICG—a charge input region ID are formed on a side of the rectangular sensing region 3. There is the other side of the sensing region adjacent to the side above-mentioned and the first potential well region FD 1, the first gate region AG, and the second potential well region FD 2 are provided in this order on the other side. All of the regions above-mentioned may be aligned in series, accordingly. FIG. 1 shows cross-sectional structure taken along the line I-I of FIG. 2.

In the above, the second gate region ICG adjusts the amount of charges supplied from the charge input region ID to the sensing region 3, and the first gate region AG adjusts the charge held in the first potential well region FD 1 to the second potential well region FD 2. The charge accumulation region 5 is comprised of the first potential well region FD 1, the first gate region AG, and the second potential well region FD 2.

In the second potential well region FD 2, a reset gate RG for discharging the charge accumulated in the second potential well region FD 2 and a charge amount detection unit 9 for detecting the accumulated charge amount are connected. A conventional circuit can be adopted for the reset gate RG and the charge amount detection unit 9, respectively.

Figure 3:
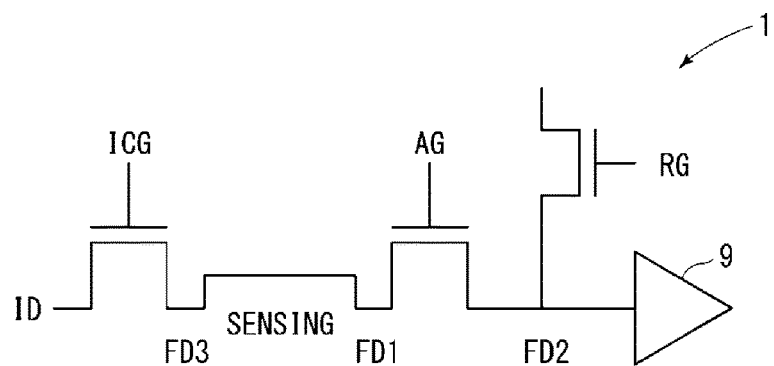
FIG. 3 is a circuit diagram of the pH sensor 1.

FIG. 3 shows a circuit diagram of the pH sensor 1.

The charge input region ID and the first to third potential well regions FD 1 to FD 3 are doped with n-type dopants. Before forming the silicon oxide insulating film 11, the doping is performed by implanting the n-type dopants by masking the surface of the semiconductor substrate 10. It is preferable that the doping conditions for the charge input region ID and the first to third potential well regions FD 1 to FD 3 be the same to minimize the number of times of mask processing. As a result, the same dopant is introduced into these four layers at the same concentration by one doping treatment.

According to the pH sensor 1 shown in FIG. 1, even if the silicon nitride layer 13 exists on the side surface of the ICG electrode 15, the potential barrier is not formed because the potential of the third potential well region FD 3 is higher than that of the sensing region and the third potential well region FD 3 is positioned in the substrate opposing the silicon nitride layer 13 on the side surface of the ICG electrode 15.

The third potential well region FD 3 is so designed that the silicon nitride film 13, covering the sensing-region side surface of the ICG electrode 15, is inside of the third potential well region FD 3 as projecting the silicon nitride film 13 onto the third potential well region FD 3 in the lower part of FIG. 1.

The width of the third potential well region FD 3 can be arbitrarily set in consideration of etching conversion difference and mask shift. In this embodiment, the width of the third potential well region FD 3 is set to 1.20 µm under the 2.0 µm process (that is, the minimum channel length is 2.0 µm).

Figure 4:
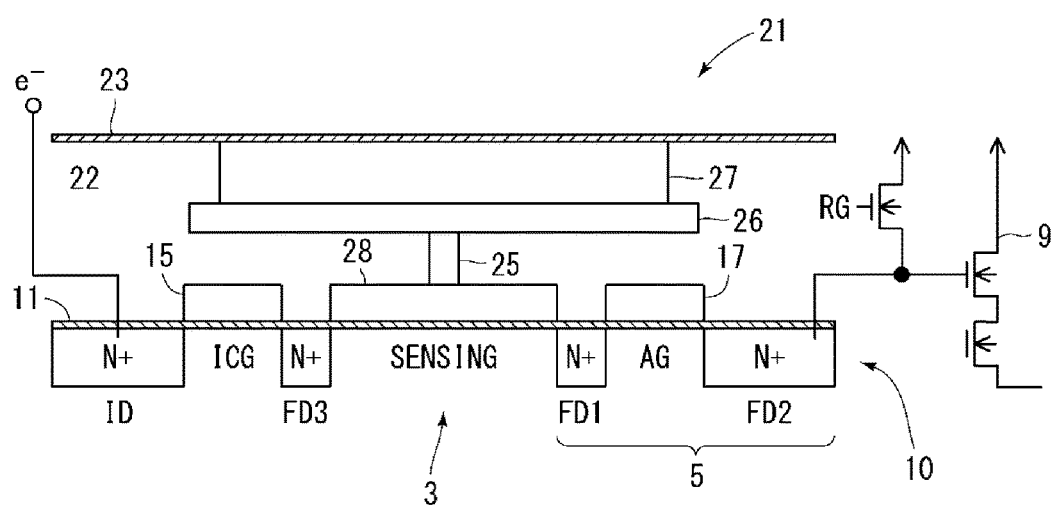
FIG. 4 is a cross-sectional view showing a configuration of a pH sensor 21 as a modified embodiment.

FIG. 4 shows an extended type pH sensor 21.

The same elements as those in FIG. 1 are denoted by the same reference numerals, and a description thereof will be partially omitted.

The direct type pH sensor 1 of FIG. 1 and the pH sensor 21 of FIG. 4 adopt the same configuration in the semiconductor substrate 10, and are different in the structure stacked via the silicon oxide insulation layer 22.

In the pH sensor 21 shown in FIG. 4, a silicon oxide insulation layer 22 is laminated on the entire surface of the silicon oxide insulation film 11, and a silicon nitride film 23 as a sensitive film is laminated on the surface of the silicon oxide layer 22. The potential change of the silicon nitride film 23 is transmitted to the sensing region defining electrode 28 via the conductive layers 25, 26, 27 made of a metal material or the like buried in the silicon oxide insulation layer 22. A tantalum pentoxide film can also be used as the sensitive layer 23.

As a result, the potential of the silicon nitride layer 23 corresponding to the pH of the measurement object is reflected on the potential of the sensing region 3.

It is to be noted that the extended type pH sensor 21 shown in FIG. 4 can be formed by a well-known process and, of course, the silicon oxide insulation layer can also be formed in multiple layers (see Japanese Patent Application Laid-Open No. 2010-535360 and is incorporated herein by reference).

Next, the operation of the pH sensor 1 will be described with reference to FIG. 5. The operation of the pH sensor 21 shown in FIG. 4 is also the same.

In the standby state (not shown), the reset gate RG connected to the second potential well region FD 2 has a high potential and charges in the second potential well region FD 2 are discharged to the outside.

(1) Charge Filling Step

In FIG. 5A, the potential of the first gate AG region is made sufficiently lower than that of the sensing region 3, charges are supplied from the charge input region ID, and the first potential well region FD 1 is filled with charges. At this time, the potential of the second gate region ICG is sufficiently higher than the sensing region 3, and this state of the second gate region is maintained thereafter.

(2) Sensing Step

In FIG. 5B, the potential of the charge input region ID is increased to discharge electrons. As a result, electrons in the sensing region 3 are also discharged from the charge input region ID side, and charges are left only in the first potential well region FD 1 (see FIG. 5C). Here, since the third potential well region FD 3 is formed, no potential barrier is generated between the sensing region 3 and the second gate region, and the electrons in the sensing region 3 are completely removed, and it remains Absent.

At this time, the lowest potential (boundary potential) of electrons existing in the first potential well region FD 1 is equal to the potential of the sensing region 3.

(3) Charge Accumulation Step

In FIG. 5D, the potential of the first gate region AG is raised to a predetermined value to transfer electrons present in the first potential well region FD 1 to the second potential well region FD 2. The amount of transferred charges corresponds to the potential difference between the potential of the sensing region 3 and the predetermined potential of the first gate region AG. If the latter is fixed, the amount of transferred charges corresponds to the height of the potential of the sensing region 3.

In other words, the height of the potential of the sensing region 3 is reflected in the amount of electrons accumulated in the second potential well region FD 2 (FIG. 5E).

Figure 5:
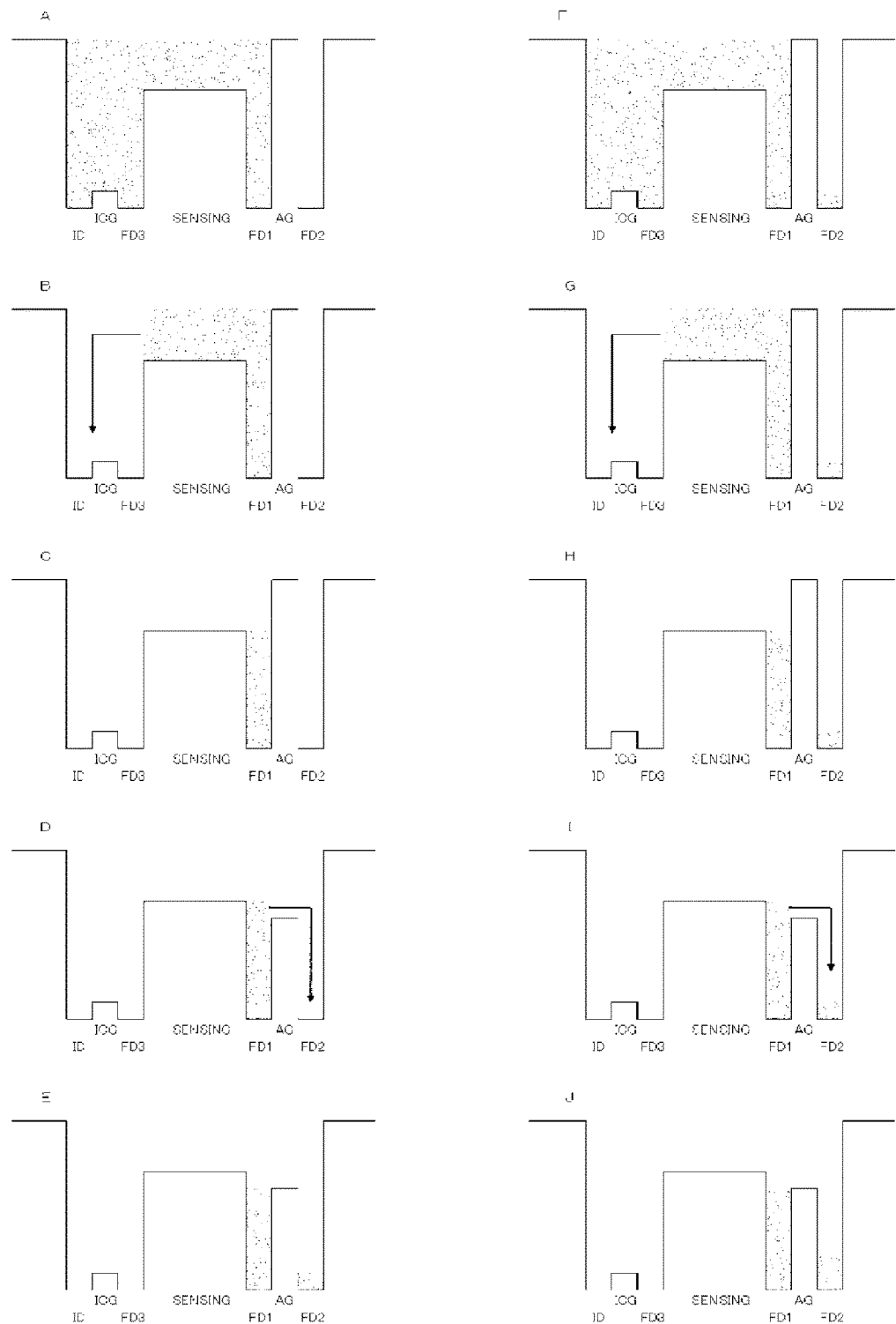
FIG. 5 shows operation of the pH sensor 1 of the first embodiment.

As keeping the electrons accumulated in the second potential well region FD 2, the above steps (1) to (3) are repeated (see FIGS. 5F to 5 I). As a result, as shown in FIG. 5J, electrons are accumulated in the second potential well region FD 2.

Since the electron accumulated in the second potential well region FD 2 corresponds to the potential of the sensing region 3 (that is, the pH value of the detection object) as described above, the electrons accumulated in the second potential well region FD 2 are detected by the charge amount detection unit 9, and the pH of the measurement object is specified.

Thereafter, the electrons in the second potential well region FD 2 are discharged via the reset gate RG and returns to the standby state.

According to the pH sensor 1 of the embodiment configured as described above, it is possible to measure the pH value of the object to be detected without forming any potential pool in the sensing region 3.

Figure 6:
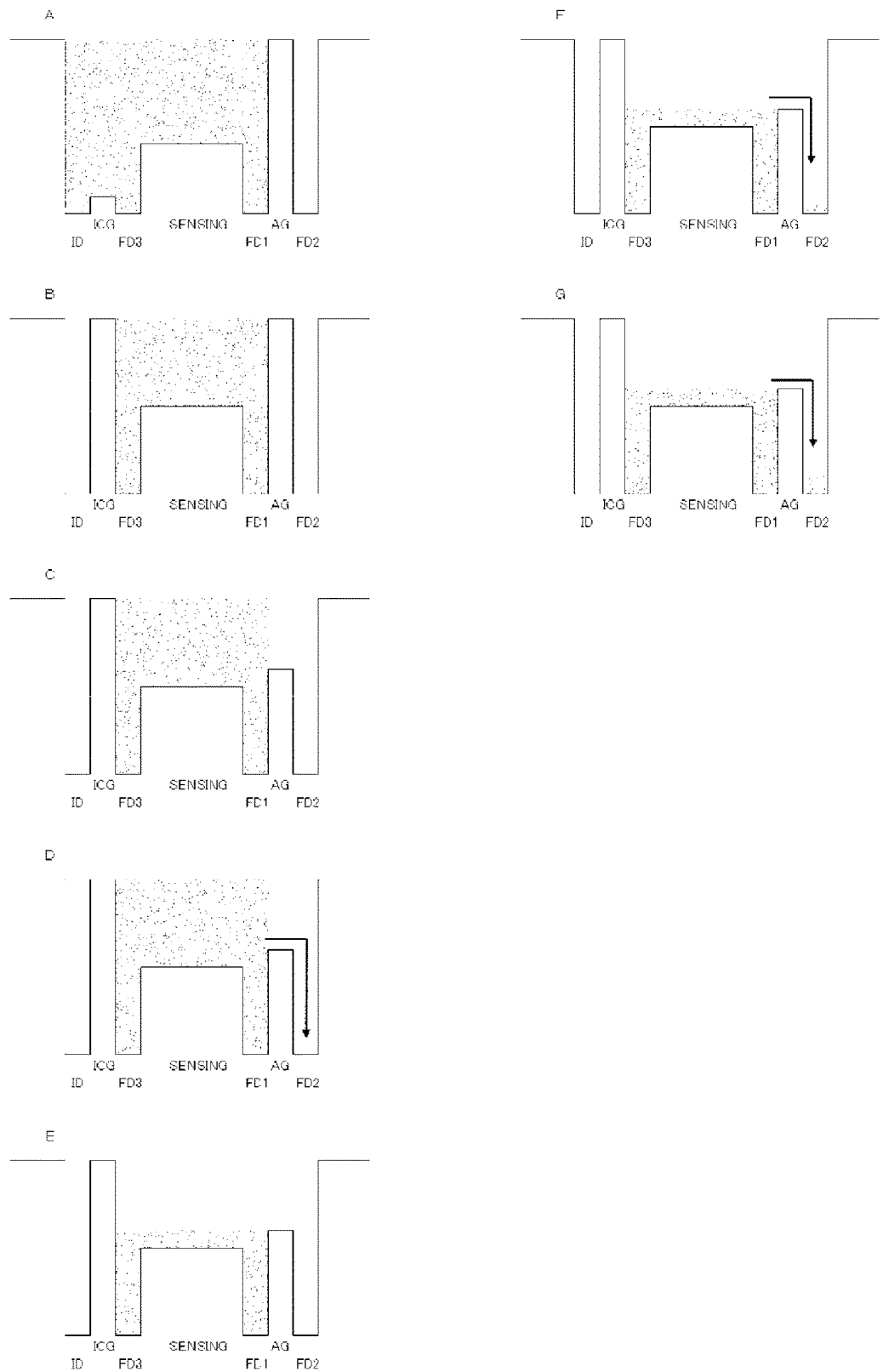
FIG. 6 shows that the pH sensor 1 of the first embodiment operates as an optical sensor.

The operation of the pH sensor 1 of FIG. 1 as an optical sensor will be described with reference to FIG. 6.

(6-1) Preparatory Step

In FIG. 6A, the potential of the first gate region AG is made sufficiently lower than that of the sensing region 3 from the standby state (a state where the second potential well region FD 2 is empty), charges are supplied from the charge input region ID to fill the first potential well region FD 1 with the charges. At this time, the potential of the second gate region ICG is sufficiently higher than that of the sensing region 3.

In FIG. 6B, the potential of the second gate region ICG is lowered to separate the charge input region ID from the third potential well region FD 3 and prohibit movement of electrons there between. Thereafter, the charges of the charge input region ID are discharged.

Next, as shown in FIG. 6C, the potential of the first gate region AG increases. The electrons having potential lower than the potential of the first gate region AG in the third potential well region FD 3, in the sensing region 3 and in the first potential well region FD 1 are transferred to the second potential well region FD 2. At this time, the potential of the first gate region AG is made lower than or equal to the potential of the sensing region 3.

Thereafter, the electrons in the second potential well region FD 2 are discharged to the outside via the reset gate RG (FIG. 6E).

(6-2) Sensing Step

In this state, for example, when the shutter is opened and light is made incident on the sensing region 3, the incident light generates electrons corresponding to the incident light in the depletion layer region formed under the sensing region and its vicinity. The electrons thus generated cross over the first gate region AG and are accumulated in the second potential well region FD 2 (FIGS. 6E to 6 G).

In this manner, the amount of electrons accumulated in the second potential well region FD 2 is detected, and the amount of light having been incident on the sensing region is specified. After that, the electrons in the second potential well region FD 2 are discharged via the reset gate RG and return to the standby state.

The potential of the first gate region AG the potential of the sensing region 3. Here, it is more preferable that the potential of the first gate region AG be lower than the potential of the sensing region 3. This is because, for example, the potential barrier, generated when the third potential well region FD 3 is omitted, can be submerged in the electronic pool formed on the sensing region 3.

Figure 7:
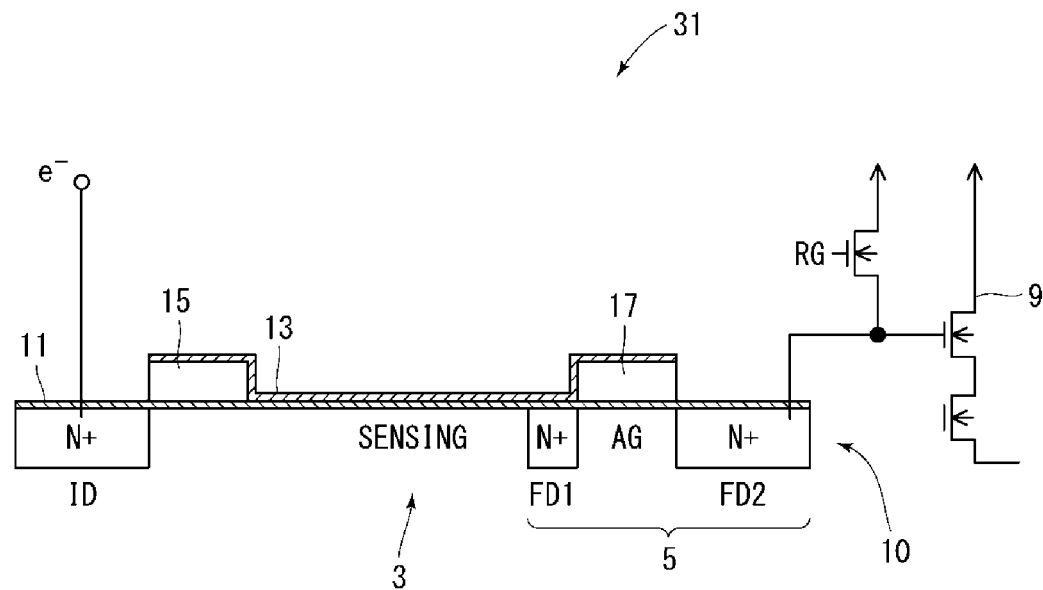
FIG. 7 is a cross-sectional view showing a configuration of a pH sensor 31 according to a second embodiment of the present invention.
Figure 8:
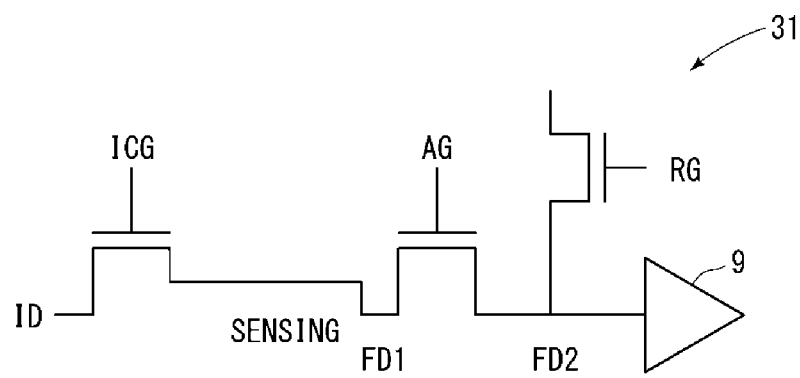
FIG. 8 is a circuit diagram of a pH sensor 31.

FIG. 7 shows a pH sensor 31 of another embodiment. FIG. 8 is a circuit diagram thereof. This pH sensor 31 is obtained by omitting the third potential well region FD 3 from the pH sensor 1 shown in FIG. 1. In the pH sensor 31, the same elements as those of the pH sensor 1 shown in FIG. 1 are denoted by the same reference numerals, and description thereof is omitted.

In the pH detection operation of the pH sensor 31, operations of the charge input region ID, the second gate region ICG, the first gate region AG, the charge amount detection unit 9, and the reset gate RG are the same as those in FIG. 5

Figure 9:
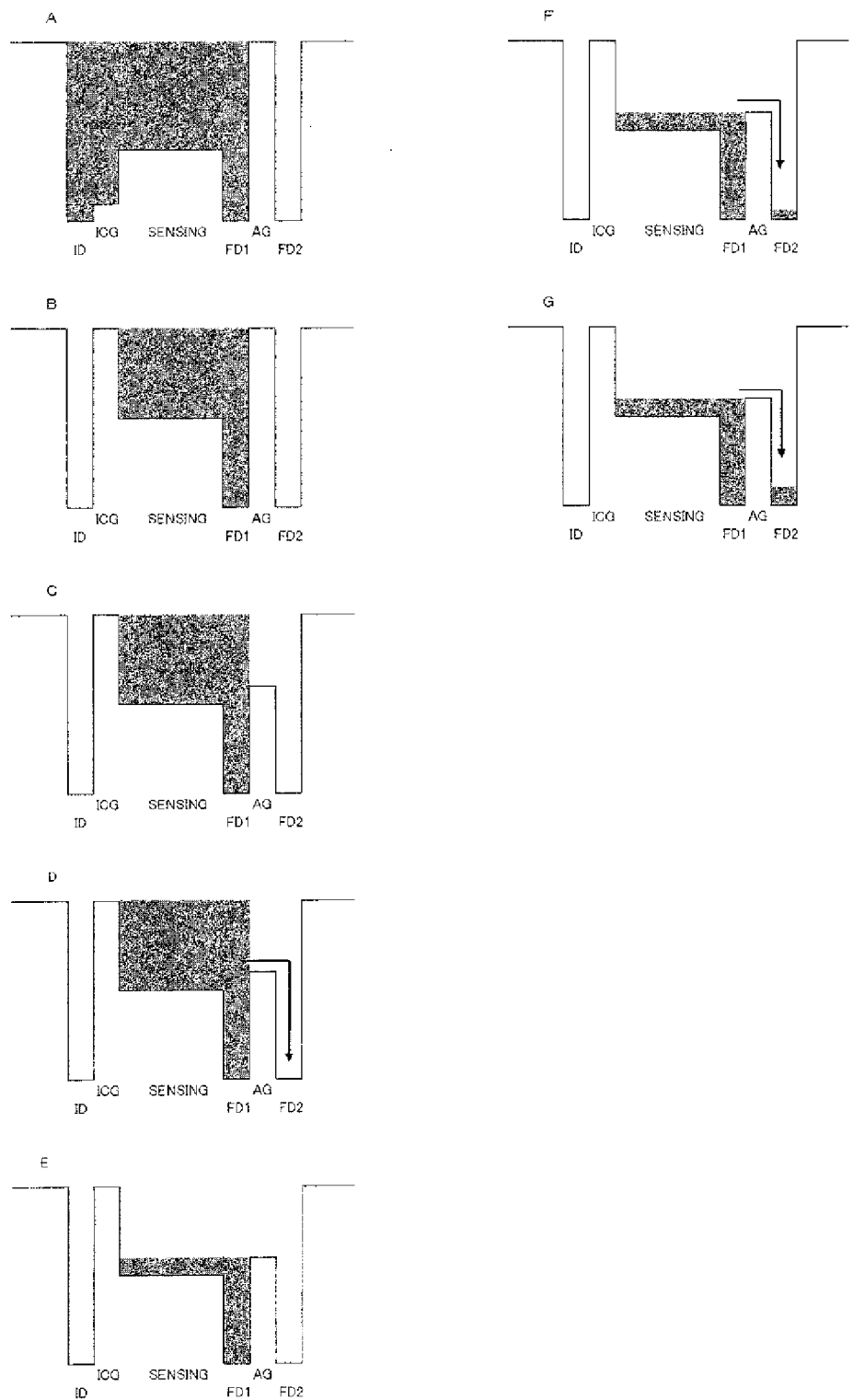
FIG. 9 shows operation of the pH sensor 31.

The operation of this pH sensor 31 as a light sensor is shown in FIG. 9

In FIGS. 9A to 9G, operations of the charge input region ID, the second gate region ICG, the first gate region AG, the charge amount detection unit 9, and the reset gate RG are all same with the operations described with reference to FIGS. 6A to 6G.

Figure 10:
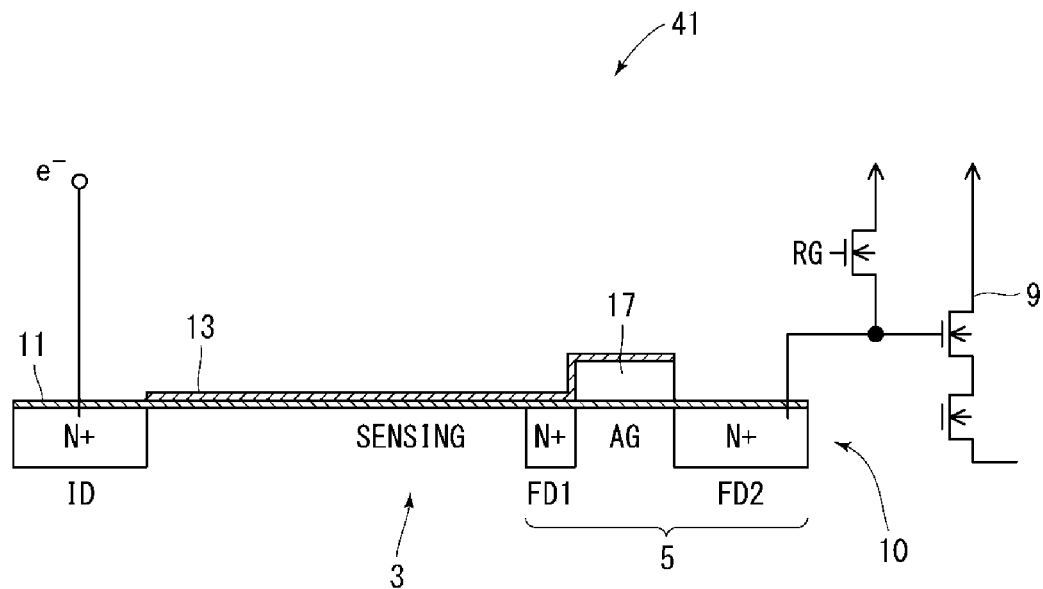
FIG. 10 is a cross-sectional view showing a configuration of a pH sensor 41 according to a third embodiment of the present invention.
Figure 11:
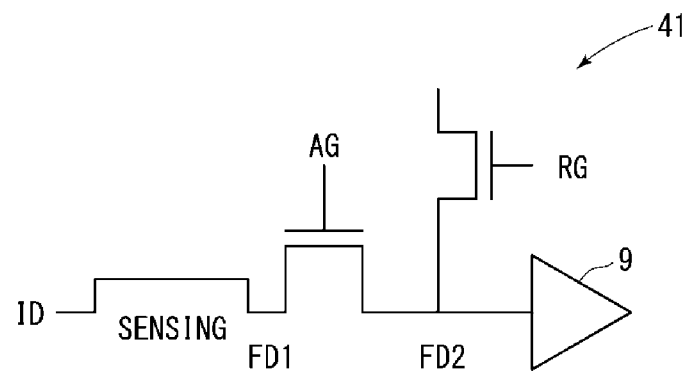
FIG. 11 is a circuit diagram of a pH sensor 41.

FIG. 10 shows a pH sensor 41 according to another embodiment. FIG. 11 is a circuit diagram thereof.

This pH sensor 41 is obtained by omitting the second gate region ICG and the third potential well region FD 3 from the pH sensor 1 shown in FIG. 1. In the pH sensor 41, the same elements as those of the pH sensor 1 shown in FIG. 1 are denoted by the same reference numerals, and description thereof is omitted.

The pH sensor 41 configured as described above is suitable for high density integration since the ICG electrode 15 can be omitted as compared with the pH sensor 1 shown in FIG. 1.

Figure 12:
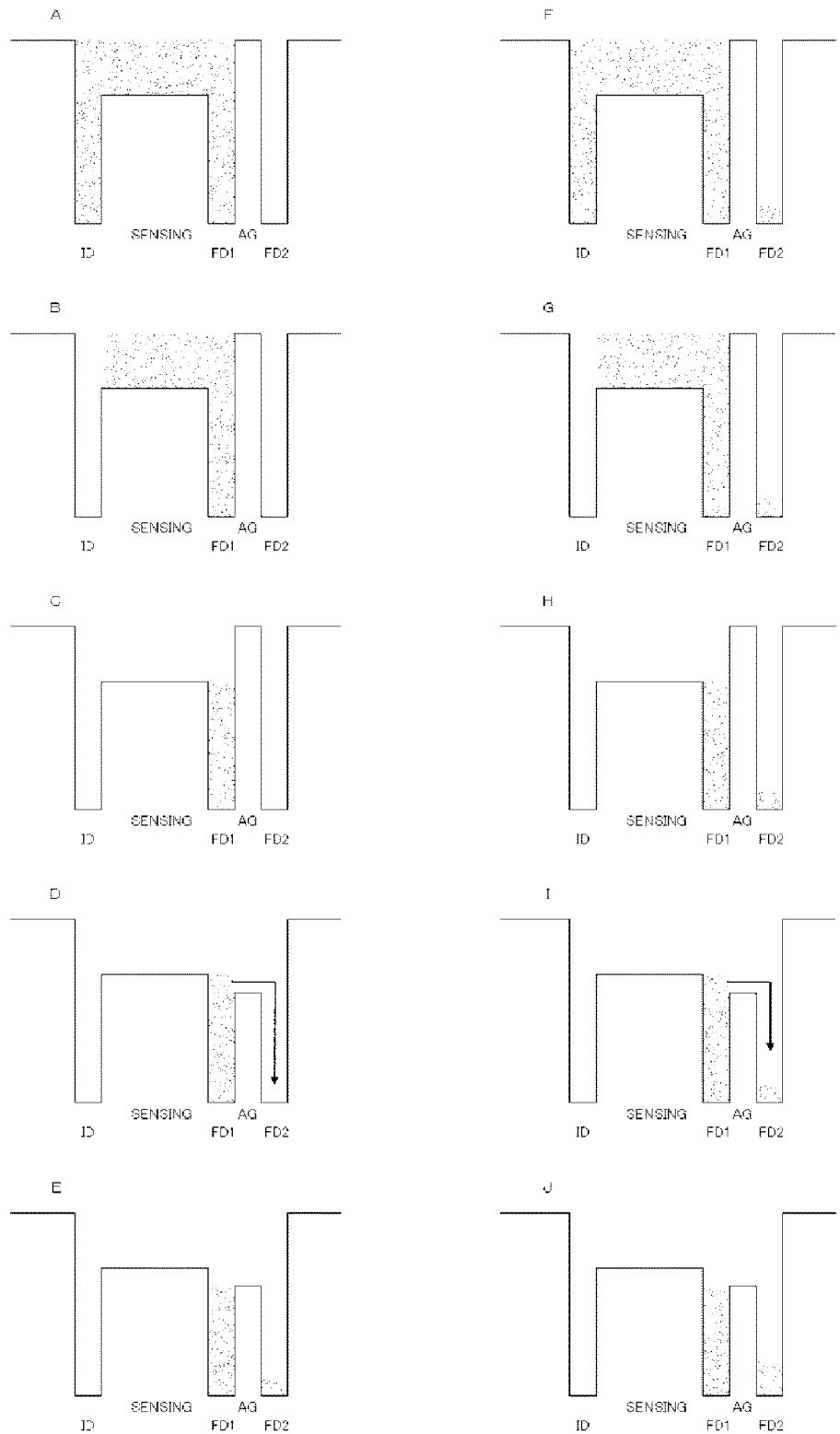
FIG. 12 shows operation of the pH sensor 41.

The pH detection operation of the pH sensor 41 is shown in FIG. 12.

In the standby state (not shown), the reset gate RG connected to the second potential well region FD 2 has a high potential and the charge in the second potential well region FD 2 is discharged to the outside.

(1) Charge Filling Step

In FIG. 12A, the potential of the second gate region AG is made sufficiently lower than that of the sensing region 3, electrons are supplied from the charge input region ID, and the first potential well region FD 1 is filled with electrons.

(2) Sensing Step

In FIG. 12B, the potential of the charge input region ID is increased to discharge electrons. As a result, electrons in the sensing region 3 are also discharged from the charge input region ID side, and electrons are left only in the first potential well region FD 1 (see FIG. 12C). At this time, the lowest potential (boundary potential) of electrons existing in the first potential well region FD 1 is equal to the potential of the sensing region 3.

(3) Charge Accumulation Step

In FIG. 12D, the potential of the first gate region AG is raised to a predetermined potential to transfer electrons present in the first potential well region FD 1 to the second potential well region FD 2. The amount of transferred electrons corresponds to the potential difference between the potential of the sensing region 3 and the predetermined potential of the first gate region AG. If the latter is fixed, an amount of the transferred electrons depends on the height of the potential of the sensing region 3.

In other words, the height of the potential of the sensing region 3 is reflected in the amount of electrons accumulated in the second potential well region FD 2 (FIG. 12E).

Figure 13:
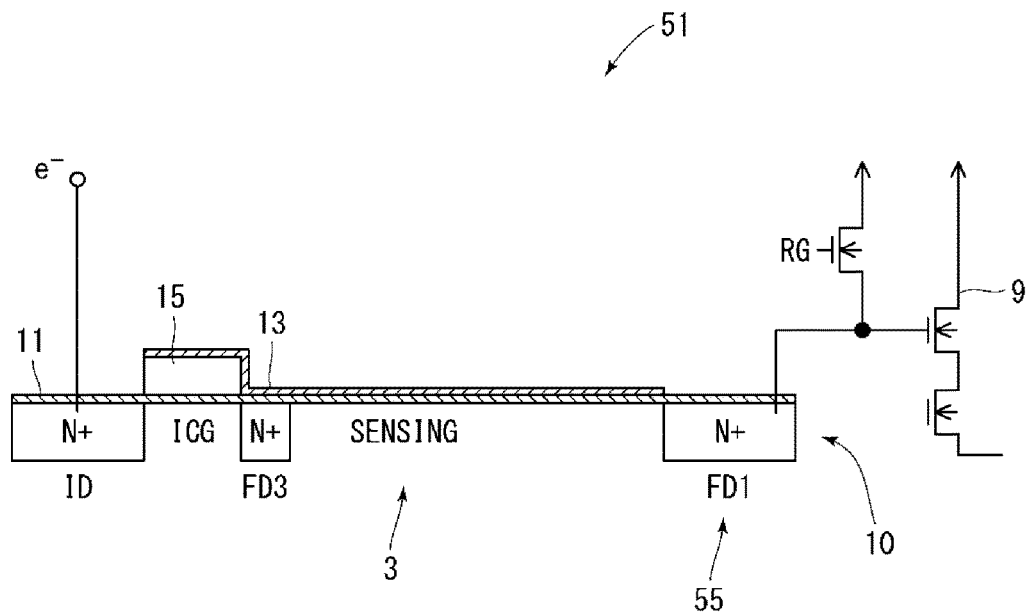
FIG. 13 is a cross-sectional view showing a configuration of a pH sensor 51 according to a fourth embodiment of the present invention.
Figure 14:
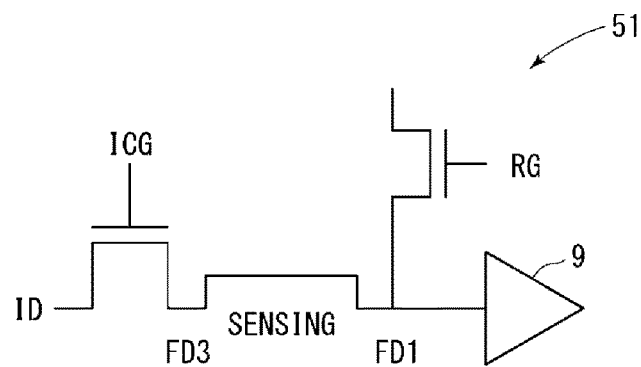
FIG. 14 is a circuit diagram of a pH sensor 51.
Figure 15:
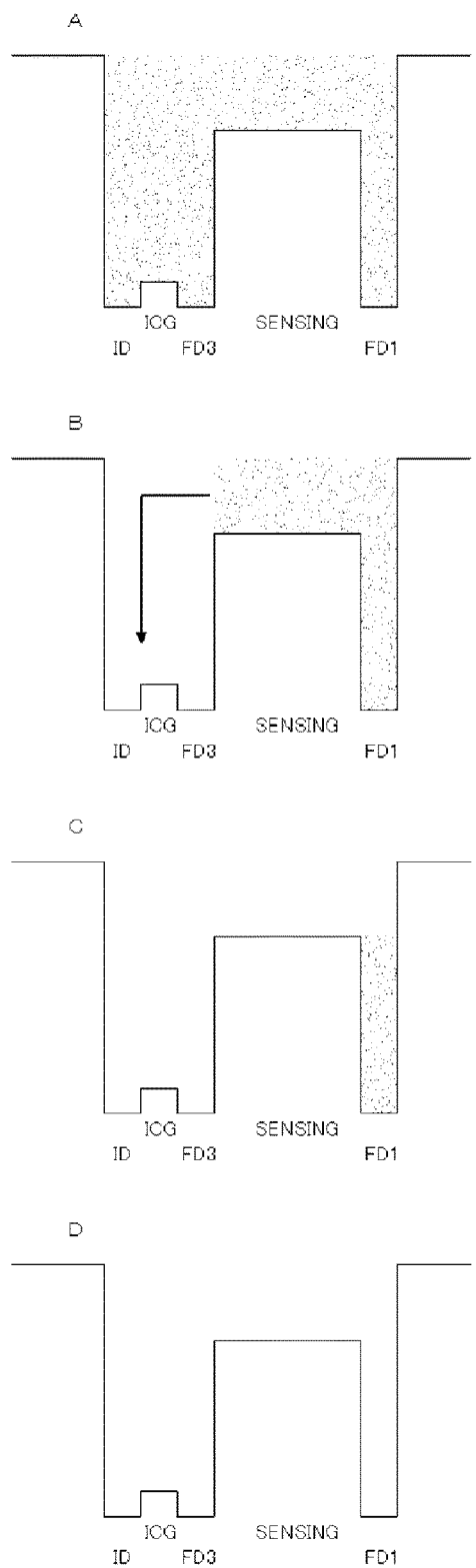
FIG. 15 shows operation of the pH sensor 51.

FIG. 13 shows a pH sensor 51 of another embodiment. FIG. 14 is a circuit diagram. This pH sensor 51 is obtained by omitting the first gate region AG and the second potential well region FD 2 from the pH sensor 1 shown in FIG. 1. In the pH sensor 51, the same elements as those of the pH sensor 1 shown in FIG. 1 are denoted by the same reference numerals, and description thereof is omitted. In this example, the first potential well region FD 1 is the charge accumulation region 55. The pH detection operation of the pH sensor 41 is shown in FIG. 15.

(1) Charge Filling Step

In FIG. 15A, charges are supplied from the charge input region ID, and the first potential well region FD 1 is filled with charges. At this time, the potential of the second gate region ICG is sufficiently higher than that of the sensing region 3, and this state is maintained thereafter.

(2) Sensing Step

In FIG. 15B, the potential of the charge input region ID is raised and electrons are discharged. As a result, electrons in the sensing region 3 are also discharged from the charge input region ID side, and charges are left only in the first potential well region FD 1 (see FIG. 15C). Here, since the third potential well region FD 3 is present, a potential barrier is not generated between the sensing region 3 and the second gate region ICG, so that electrons in the sensing region 3 are completely removed and no electron remains.

At this time, the lowest potential (boundary potential) of electrons existing in the first potential well region FD 1 is equal to the potential of the sensing region 3.

Since the maximum potential (the bottom potential in the figure) of the first potential well region FD 1 is fixed (depending on the type and amount of impurities), the amount of electrons that can exist in the first potential well region FD 1 depends on the potential of the sensing region 3.

In other words, the height of the potential of the sensing region 3 is reflected in the amount of electrons accumulated in the first potential well region FD 1.

(3) Charge Amount Detection Step

The amount of electrons present in the first potential well region FD 1 is detected by the electron amount detection unit 9, and the pH value is specified. Thereafter, the reset gate RG is operated to discharge the electrons in the first potential well region FD1, and the standby state is set (see FIG. 15D).

In the pH sensor 51 configured as described above, the ICG electrode 15 is omitted as compared with the pH sensor 1 shown first, and as a result, transistors for controlling the electrode and wirings related thereto can be omitted, so that the pH sensor 51 is preferable in high density integration.

Figure 16:
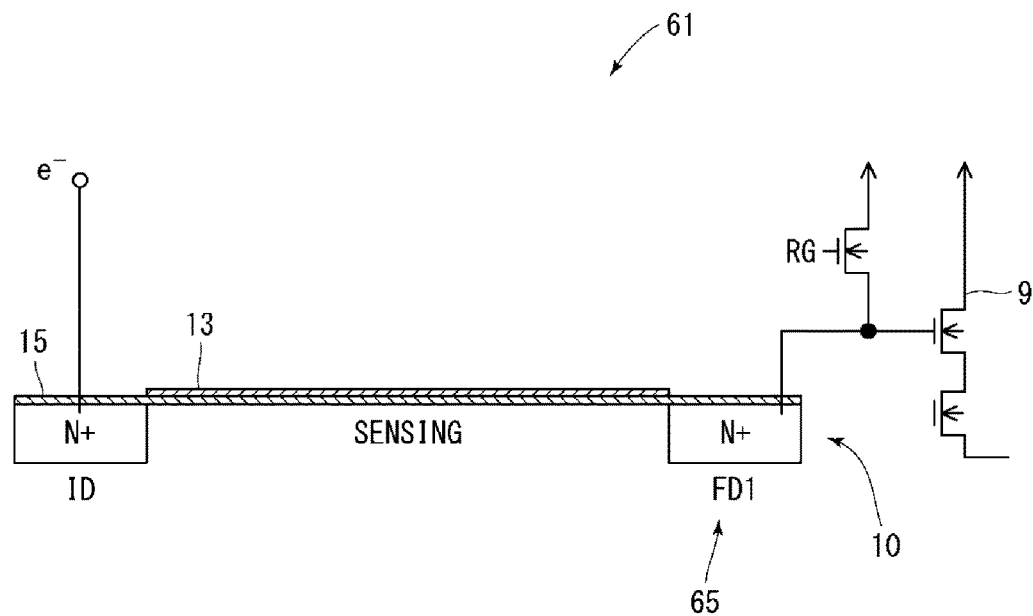
FIG. 16 is a cross-sectional view showing a configuration of a pH sensor 61 according to a fifth embodiment of the present invention.
Figure 17:
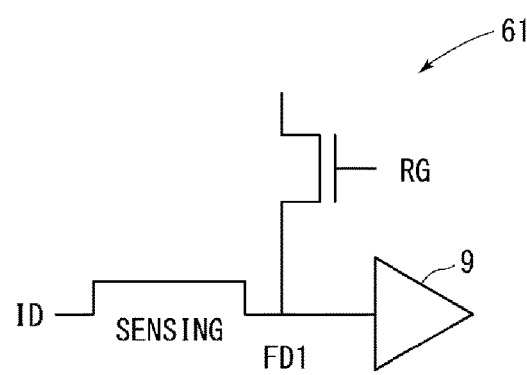
FIG. 17 is a circuit diagram of a pH sensor 61.

FIG. 16 shows a pH sensor 61 of another embodiment. FIG. 17 is a circuit diagram thereof.

This pH sensor 61 is obtained by omitting the first gate region AG and the second potential well region FD 2 and the second gate region ICG and the third potential well region FD 3 from the pH sensor 1 shown in FIG. 1. In the pH sensor 61, the same elements as those of the pH sensor 1 shown in FIG. 1 are denoted by the same reference numerals, and description thereof is omitted. In this example, the first potential well region FD 1 is the charge accumulation region 65.

Figure 18:
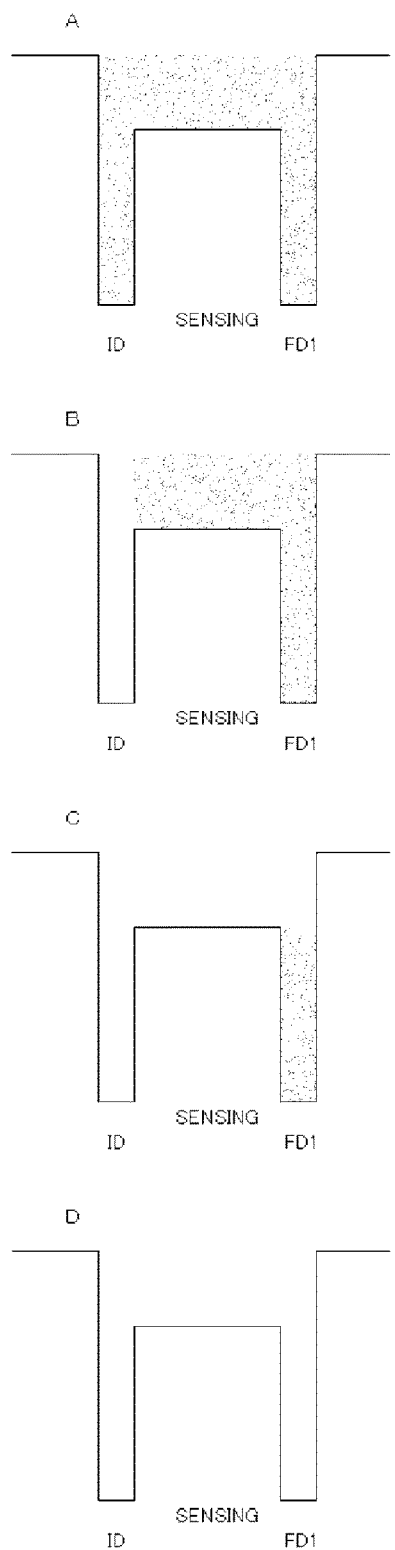
FIG. 18 shows operation of the pH sensor 61.

The pH detection operation of the pH sensor 61 is shown in FIG. 18.

In a standby state (not shown), the reset gate RG connected to the first potential well region FD 1 has a high potential, and the charges in the first potential well region FD 1 are discharged to the outside.

(1) Charge Filling Step

In FIG. 18A, charges are supplied from the charge input region ID, and the first potential well region FD 1 is filled with charges.

(2) Sensing Step

In FIG. 18B, the potential of the charge input region ID is raised to discharge electrons. As a result, electrons in the sensing region 3 are also discharged from the charge input region ID side, and charges are left only in the first potential well region FD 1 (see FIG. 18C).

At this time, the lowest potential (boundary potential) of electrons existing in the first potential well region FD 1 is equal to the potential of the sensing region 3.

Since the maximum potential (the bottom potential in the figure) of the first potential well region FD 1 is fixed (depending on the type and amount of impurities), the amount of electrons that can exist in the first potential well region FD 1 depends on the potential of the sensing region 3.

In other words, the height of the potential of the sensing region 3 is reflected in the amount of electrons accumulated in the first potential well region FD 1.

(3) Charge Amount Detection Step

The amount of electrons present in the first potential well region FD 1 is detected by the electron amount detection unit 9, and the pH value is specified. Thereafter, the reset gate RG is operated to discharge the electrons in the first potential well region FD 1, and the standby state is set (see FIG. 18D).

As compared with the pH sensor 1 shown in FIG. 1, two electrodes (ICG electrode 15, AG electrode) are absent in the pH sensor 61 configured as described above, and as a result, an electronic device for controlling these electrodes and wirings related thereto can be omitted. The pH sensor 62, therefor, is suitable for high density integration.

Figure 19:
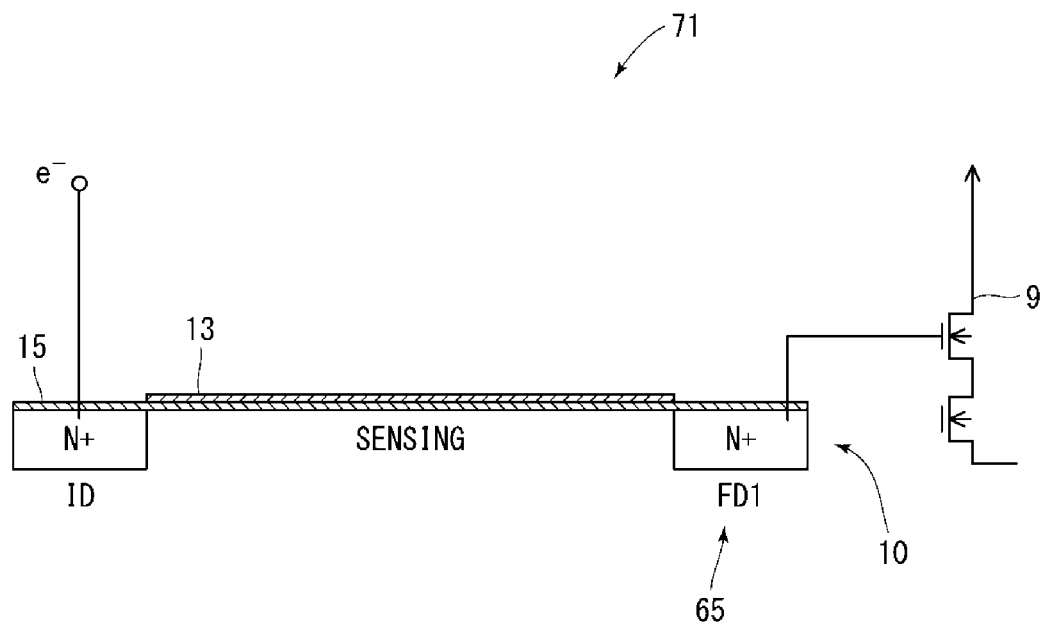
FIG. 19 is a cross-sectional view showing a configuration of a pH sensor 71 according to a sixth embodiment of the present invention.
Figure 20:
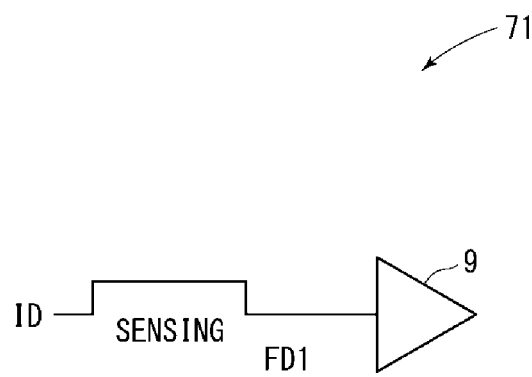
FIG. 20 is a circuit diagram of a pH sensor 71.

FIG. 19 shows a pH sensor 71 according to another embodiment. FIG. 20 is a circuit diagram thereof.

This pH sensor 71 is obtained by omitting the reset gate RG from the pH sensor 61 shown in FIG. 16. In the pH sensor 71, the same elements as those of the pH sensor 61 shown in FIG. 16 are denoted by the same reference numerals, and description thereof is omitted.

Figure 21:
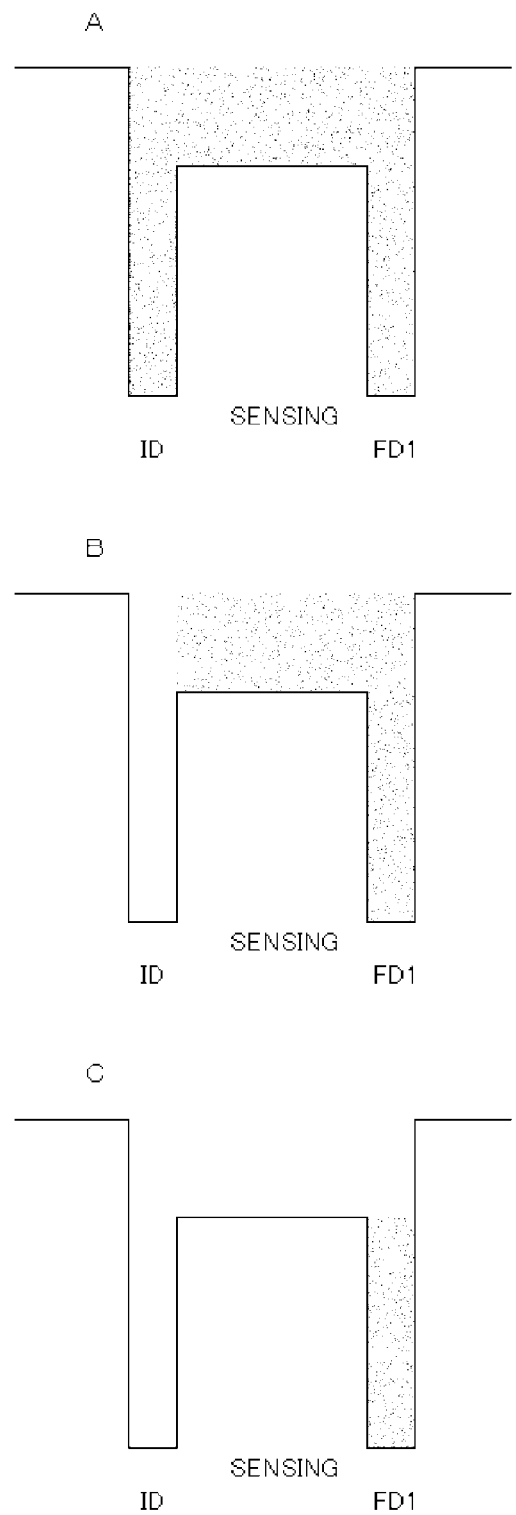
FIG. 21 shows operation of the pH sensor 71.

The pH detection operation of the pH sensor 71 is shown in FIG. 21

(1) Charge Filling Step

In FIG. 21A, charges are supplied from the charge input region ID, and the first potential well region FD 1 is filled with charges.

(2) Sensing Step

In FIG. 21B, the potential of the charge input region ID is increased to discharge electrons. As a result, the electrons in the sensing region 3 are also discharged from the charge input region ID side, and charges are left only in the first potential well region FD 1 (see FIG. 21C).

At this time, the lowest potential (boundary potential) of electrons existing in the first potential well region FD 1 is equal to the potential of the sensing region 3.

Since the maximum potential (the bottom potential in the figure) of the first potential well region FD 1 is fixed (depending on the type and amount of impurities), the amount of electrons that can exist in the first potential well region FD 1 depends on the potential of the sensing region 3.

In other words, the height of the potential of the sensing region 3 is reflected in the amount of electrons accumulated in the first potential well region FD 1.

(3) Charge Amount Detection Step

The amount of electrons present in the first potential well region FD 1 is detected by the electron amount detection unit 9, and the pH value is specified.

In the pH sensor 61 of FIG. 16, the charges accumulated in the first potential well region FD 1 are discharged by the reset gate RG, but such a discharging operation is omitted in the pH sensor 71. That is, in a state where charges are stored in the first potential well region FD 1, charges are supplied from the charge input region ID to realize the state of FIG. 21A.

The pH sensor 71 configured as described above is more suitable for higher integration because the reset gate RG is absent as compared with the pH sensor 61 shown in FIG. 16. In addition, since the step of discharging electric charge is omitted, it is also suitable for high speed operation.

Also in the pH sensor 51 shown in FIG. 13, the reset gate RG can be omitted similarly to the above.

The present invention is not limited to the description of the embodiment and examples of the invention at all. Various modifications are also included in the present invention as long as they can be easily conceived by those skilled in the art without departing from the spirit of the scope of claims.

EXPLANATION OF NUMERAL NUMBERS IN FIGS.

1, 21, 31, 41, 51, 61, 71 Chemical/physical phenomena detection device (pH sensor)
3 Sensing region
5, 45, 55 Charge accumulation region
9 Charge amount detection unit
10 Semiconductor substrate
11 Silicon oxide film (insulating film)
13 Silicon nitride film (sensitive film)
15 ICG electrode
17 AG electrode
ID Charge input region
ICG Second gate region (input charge control region)
AG First gate region
FD 1 to FD 3 First potential well region to third potential well region
RG Reset gate

The invention claimed is:

1. A method for controlling chemical or physical phenomenon detecting device, wherein the device comprises a semiconductor substrate in which a sensing region and a charge accumulation region are partitioned, a potential of the sensing region changes in accordance with a change in an external environment, and an amount of charges reflecting the potential of the sensing region is accumulated in the charge accumulation region and the accumulated charges are detected
   wherein the charge accumulation region comprises a first potential well region continuous with the sensing region, a second potential well region, and an analog gate region positioned between the first potential well region and the second potential well region,
   wherein the semiconductor substrate further comprises a charge input region for supplying charges to the sensing region, and
   an input charge control region formed between the charge input region and the sensing region to adjust the supply of charges from the charge input region to the sensing region, and the sensing region has photosensitivity,
   the method comprising:
      a sensing step for making the boundary potential of charges in the first potential well region equal to the potential of the sensing region; and
      a step for making setting absolute potential values of the analog gate region and the input charge control region such that the input charge control region <the analog gate region ≤the sensing region,
      a step for transferring charges generated in response to incident light in the sensing region to the second potential well region via the analog gate region, and
      a detecting step for detecting an amount of the charges held in the first potential well region in the sensing step.

2. A chemical or physical phenomenon detecting device comprising a semiconductor substrate containing a sensing region and a charge accumulation region, wherein:
   the charge accumulation region comprises a first potential well region which is adjacent to, and spatially contiguous with, the sensing region;
   an electrical potential of the sensing region changes in response to a change in an external environment in communication with the sensing region;
   the sensing region and accumulation region are jointly configured and arranged such that, when a boundary electrical potential of the first potential well is equal to the electrical potential of the sensing region, an amount of charge corresponding to the electrical potential of the sensing region collects in the accumulation region in the absence of any voltage externally applied to any of the first potential well and the sensing region; and an electrical signal corresponding to the amount of charge collected in the accumulation region is produced at an electrical output terminal of the device.

3. A chemical or physical phenomenon detection device according to claim 2, wherein the charge accumulation region further includes:
   a second potential well region, and an analog gate region positioned between the first potential well region and the second potential well region;
   wherein the first and second potential well regions are jointly configured and arranged such that the amount of charge collected in the accumulation region is transferred from the first potential well region to the second potential well region by adjusting the electric potential of the analog gate region; and
   wherein the electrical signal corresponding to the amount of charge collected in the accumulation region is produced according to an amount of charge collected in the second potential well.

4. A chemical or physical phenomenon detection device according to claim 2 wherein the semiconductor substrate further contains:
   a charge input region for supplying charges to the sensing region;
   an input charge control region formed between the charge input region and the sensing region to adjust the supply of charges from the charge input region to the sensing region; and
   a third potential well region positioned between the input charge control region and sensing region and formed adjacent to, and contiguous with, the sensing region.

5. A method of measuring a chemical or physical phenomenon using a chemical or physical phenomenon detecting device wherein:
   the device comprises a semiconductor substrate containing a sensing region, a charge accumulation region, and an electrical output terminal;
   the charge accumulation region comprises a first potential well region which is adjacent to, and spatially contiguous with, the sensing region;
   an electrical potential of the sensing region changes in response to a change in an external environment in communication with the sensing region; and
   the sensing region and accumulation region are jointly configured and arranged such that, when a boundary electrical potential of the first potential well is equal to the electrical potential of the sensing region, an amount of charge corresponding to the electrical potential of the sensing region collects in the accumulation region in the absence of any voltage externally applied to any of the first potential well and the sensing region;

the method comprising:
   (i) during a sensing step, configuring the electrical boundary potential of the first potential well to equal the electrical potential of the sensing region; and
   (ii) during a detection step following the sensing step, producing an electrical signal corresponding to the amount of charge collected in the accumulation region at the electrical output terminal of the device.

6. A method of measuring a chemical or physical phenomenon using a chemical or physical phenomenon detecting device according to claim 5 wherein the sensing region is sensitive to light;
   wherein the sensing step further includes configuring respective absolute potential values of the analog gate region and the input charge control region such that an electric potential of the input charge control region <an electric potential of the analog gate region ≤the electrical potential of the sensing region, and
   wherein the method further includes, after the sensing step and before the detection step, transferring charges generated in response to incident light in the sensing region to the second potential well region via the analog gate region.

* * * * *